(12) United States Patent
Chen et al.

(10) Patent No.: US 7,404,975 B2
(45) Date of Patent: Jul. 29, 2008

(54) MORINGA CRUDE EXTRACTS AND THEIR DERIVED FRACTIONS WITH ANTIFUNGAL ACTIVITIES

(75) Inventors: Hueih Min Chen, Shien Tein (TW); Ping-Hsien Chuang, Taipei (TW)

(73) Assignee: Academia Sinica, Nankang, Taipei (TW)

( * ) Notice: Subject to any disclaimer, the term of this patent is extended or adjusted under 35 U.S.C. 154(b) by 0 days.

(21) Appl. No.: 11/431,234

(22) Filed: May 10, 2006

(65) Prior Publication Data

US 2007/0264366 A1    Nov. 15, 2007

(51) Int. Cl.
*A61K 36/00* (2006.01)
(52) U.S. Cl. .................................... 424/774
(58) Field of Classification Search ........ None
See application file for complete search history.

(56) References Cited

U.S. PATENT DOCUMENTS

| 5,929,124 | A  | * | 7/1999  | Hostettmann et al. | ....... 514/691 |
| 6,858,588 | B2 |   | 2/2005  | Khanuja et al.     |                 |
| 2002/0031558 | A1 | * | 3/2002  | Yoo              | ............. 424/653 |
| 2002/0151505 | A1 | * | 10/2002 | Fahey            | ............. 514/23 |
| 2004/0198669 | A1 | * | 10/2004 | Khanuja et al.   | ............. 514/25 |

OTHER PUBLICATIONS

Chuang et al., Anti-fungal activity of crude extracts and essential oil of *Moringa oleifera* Lam, *Bioresource Technology*, 98 (2007) 232-236.

* cited by examiner

*Primary Examiner*—Susan Hoffman
*Assistant Examiner*—Catheryne Chen
(74) *Attorney, Agent, or Firm*—Cohen Pontani Lieberman & Pavane LLP

(57) ABSTRACT

The present invention provides a method of treating fungal infection by administering a pharmaceutical composition comprising an extract of the leaf of *M. oleifera* as the sole active component.

5 Claims, 3 Drawing Sheets

(c)

MORINGA CRUDE EXTRACTS AND THEIR DERIVED FRACTIONS WITH ANTIFUNGAL ACTIVITIES

BACKGROUND OF THE INVENTION

1. Field of the Invention

The present invention relates to a method of treating fungal infection by administering a pharmaceutical composition comprising an extract of the leaf of *M. oleifera*.

2. Description of the Related Art

Many skin diseases such as tinea and ringworm, which are initiated by the infection of dermatophytes, popularly exist and cause serious problems in tropical and semitropical areas. Most people who live in these areas suffer from these diseases, which are difficult to remove permanently. In general, these fungi live in the dead, top layer of skin cells in moist areas of the body, such as between the toes, the groin, and under the breasts. These fungal infections cause only a small amount of irritation. Other types of fungal infections may be more serious. They can penetrate into the cells and cause itching, swelling, blistering and scaling. In some cases, fungal infections can cause reactions elsewhere in the body. For example, a person may develop a rash on the finger or hand after coming into contact with an infected foot. The dermatophytes, *Trichophyton*, *Epidermophyton*, and *Microsporum canis* are commonly involved in these infections. However, their clinical differentiation is difficult and therefore clinical care is required by a physician or other healthcare professional in the treatment of these diseases (Beentje, 1994). Furthermore, most antifungal creams used currently in the areas of Asia and Far East are imported and expensive. The development of new and cheaper anti-fungal agents from local raw materials, such as *Moringa* is therefore worthwhile and necessary.

*Moringa oleifera* (also called horseradish tree or drumstick tree) is a plant originally found in the Himalayan regions of India. The plant belongs to the family of Moringaceae. It is a shrub and small deciduous tree of 2.5 m to 10 m in height. When matured, the fruit becomes brown and has 10-50 seeds inside (Vlahof et al., 2002). This plant is popularly grown in Africa, the Middle East, southeastern Asia, the Pacific Islands, the Caribbean Islands, southern America and is now widely planted in Taiwan and China. In India, the leaf and fruit of *M. oleifera* were originally used as vegetables with the root acting as a substitute for horseradish in cooking. This plant was also reported to contain various amino acids, fatty acids, vitamins, and nutrients (Nesamani, 1999). The constituents of the *M. oleifera* tree such as the leaf, flower, fruit, and bark have been anecdotally used as herbal medicines in treatments for inflammation, paralysis, and hypertension. Moreover, many reports indicate that *M. oleifera* has highly potent anti-inflammatory (Ezeamuzle et al., 1996), hepato-protective (Pari and Kumar, 2002), antihypertensive (Faizi et al., 1995) and antitumor (Murakami et al., 1998) properties in humans. Also, its seed has strong coagulative and anti-microbial properties (Eilert et al., 1981). The seed oil has physical and chemical properties equivalent to that of olive oil and contains a large quantity of tocopherols (Tsaknis et al,. 1999).

The leaf extracts in rats were found to regulate thyroid status and cholesterol levels (Tahiliani et al., 2000; Ghasi, 2000). Therefore it can be developed as a useful agent to treat high cholesterol.

In recent years, *M. oleifera* has been widely planted on a large scale in Taiwan and China and many people in these regions have been using the seed of *Moringa* as a herb in oral to treat athlete's foot and tinea and found that it is very effective. There are millions of people in Taiwan and China who have these foot diseases due to the humid weather and there are not many effective medicines used currently for curing these diseases. The demands on the production from this plant are therefore expected to increase in these regions. However, currently, there are no scientific reports relating this plant to foot-diseases. Here, for the first time, we provide evidence that certain extracts from this plant have anti-fungal properties. Therefore, it is possible that economic development of these extracts may lead to cheaper/easier to use oral anti-skin disease agents in the future.

SUMMARY OF THE INVENTION

The present invention provides a method of treating fungal infection by administering a pharmaceutical composition comprising an extract of the leaf of *M. oleifera* as the sole active component. The pharmaceutical composition is preferably administered orally, topically or in the eye. The present method is especially effective in treating fungal infection caused by *Trichophyton rubrum*, *Trichophyton mentagrophytes*, *Epidermophyton floccosum*, and *Microsporum canis* (*T. rubrum*, *T. mentagrophytes*, *E. floccosum*, and *M. canis*).

The present invention also provides a method of treating fungal infection selected from the group consisting of *E. floccosum*, and *M. canis* by administering a pharmaceutical composition comprising an extract of the seed of *M. oleifera* as the sole active component. The extract may be obtained by drying and grinding the seeds of *M. oleifera*, extracting the ground seeds with ethanol, subjecting the ethanol extract with water, and subjecting the ethanol/water extract with ethyl acetate.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

Figure 1:
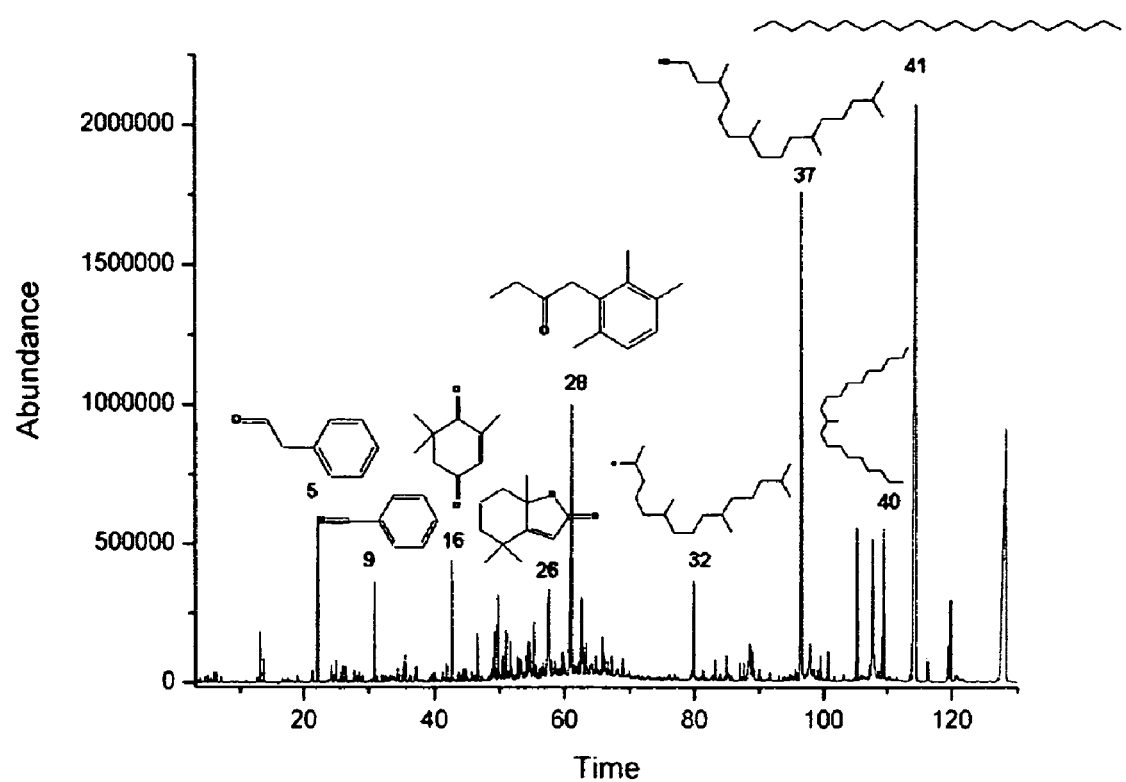
FIG. 1. A typical GC/MS spectrum of essential oil from *M. oleifera* leaf. The formulae of some typical compounds were identified from distinct peaks of the spectrum (Nos. 5, 9, 16, 26, 28, 32, 37, 40 and 41; See Table 1 for all compounds assigned with numbers).

*rubrum* include minor-axis and major-axis section views (a) before treatment with *M. oleifera* extract; (b) after treatment with 70% ethanol crude extract of *M. oleifera* seed for 24 hours; (c) more images shown after the crude extract treatment above indicating the possible cell lysis pathways of pore formation and swelling.

DETAILED DESCRIPTION OF THE PRESENTLY PREFERRED EMBODIMENTS

1. Materials and Methods 1.1 Materials and Fungal Strains.

*M. oleifera* was grown and collected from Taichung, Taiwan. The seeds were de-hulled and the seed kernels dried at 100° C. for 24 h before extraction. The leaves were freshly harvested from *M. oleifera* trees of at least one-year-old and immediately air-dried. All materials were lyophilized and powdered before experiments. The dermatophytes used in this study were obtained from the Food Industry Research and Development Institute (FIRDI) in Taiwan. *Trichophyton rubrum* (BCRC 32805), *Trichophyton mentagrophytes* (BCRC 32066), *Epidermophyton floccosum* (BCRC 30531) and *Microsporum canis* (BCRC 30541) were maintained by monthly sub-culturing on Sabouraud dextrose agar (SDA) at 28° C.

1.2 Anti-Fungal Assays

The anti-fungal assays followed the protocol (document M38-A) of The National Committee for Clinical Laboratory Standards (NCCLS) in the USA. The protocol is a standard method for broth dilution anti-fungal susceptibility testing of filamentous fungi. 100× of the drug (such as ketoconozole; the MICs of this agent tested on the fungi described above were from 0.125 µg/ml to 12.5 µg/ml ) used for the control experiment. The samples (crude extracts and fractions) were stocked in solvent DMSO in which the final concentrations of DMSO were less than 1% in the sample solution. The sample solution was further diluted to 1:10 with RPMI164O medium prior to testing. Each sample was then 1:2 diluted and divided into 10 tubes. The four strains of fungi used in this experiment were *Trichophyton rubrum*, *Trichophyton mentagrophytes*, *Epidermophyton floccosum* and *Microsporum canis*. They were grown to $10^4$ CFU per ml and then co-incubated with crude extract or essential oil samples for 72 hours at 28° C. The anti-fungal agent, ketoconazole, was used as a positive control. Numerical scores (4, no reduction in growth; 3, a slight reduction in growth or approximately 75% the growth of the growth control; 2, a prominent reduction in growth or approximately 50% the growth of the growth control; 1, a slight growth or an approximately only 25% growth relative to the growth control; 0, absence of growth) were assigned to all the sample tubes and used to indicate the amount of growth. The minimal inhibitory concentration (MIC), which is defined as the lowest concentration of an anti-microbial agent preventing the visible growth of a microorganism in an agar or broth dilution susceptibility test (numerical score 0), was determined for each test sample.

1.3 Extraction of Essential Oil.

Steam distillation and analyses were conducted as previously described (Brophy, 1991) for essential oil collection. About 16.9 g (yield=0.24%) of a clear brown essential oil was finally obtained from 7.04 kg of washed and air-dried *M. oleifera* leaves. A total amount of 500 mg of essential oil was collected. The oil was then chromatographically separated over a silica gel column (230-400 mesh, Merck) and eluted by n-hexane and diethyl ether to yield a hydrogenated fraction (named as EHF) and an oxygenated fraction (named as EOF), respectively. The EOF fraction was used in the following experiments.

1.4 Extractions of Seed and Leaf.

About 1 kg of *M. oleifera* seeds that had been powdered was extracted with one liter of 70% EtOH (repeated 5 times) and incubated for 15 days at room temperature. The yield was about 64 g per 1000 g of seed weight. 10 g of seed extract was resuspended in 250 ml of 70% EtOH and then diluted with 750 ml water. The solution was extracted (or partitioned) three times serially with n-hexane, ethylacetic acid and then n-butanol. These organic solvent extracts were then completely dried under reduced pressure. The dried sub-fractions were: seed hexane fraction (SHF), seed ethylacetic fraction (SEF), seed butanol fraction (SBF) and seed water fraction (SWF).

Washed, air-dried *M. oleifera* leaf powder (1 kg) was extracted using a similar procedure as described above for seed extraction. A total of 52 g crude extract (collected from the extraction, repeated 5 times, each time with one liter of 70% EtOH) was obtained. 10 g leaf extract was resuspended in 1000 ml 70% EtOH and decolorized with charcoal. After filtration and lyophilization, the decolorized crude extract was suspended again in 100% $ddH_2O$ (500 mL) and stirred for 10 mill. The solution was centrifuged and the supernatant collected. Subsequently, the supernatant was completely dried under reduced pressure to give two fractions: (1) a water dissoluble fraction LWF; (2) a water indissoluble fraction whose precipitate was collected and dried. This indissoluble fraction was named LEF.

1.5 Chemical Characterization of Essential Oil.

The total neutral essential oil from *M. oleifera* leaves was analyzed by an Agilent 6890N Network GC (Gas Chromatograph) system with an Agilent 5973 Network mass selective detector. The machine was equipped with a HIP-5M5 (Mass Spectroscopy) column (30 m×0.25 mm (5%-Phenyl)-methylpolysiloxane capillary column, film thickness=0.25 µm), 250° C. temperature injector and 240° C. temperature transfer line. The oven temperature was programmed as follows: initial temperature; 60° C. for 5 min, increase 2° C./min up to 150° C., 10 min at 150° C., and then increase 2° C./min up to 220° C., 30 min at 220° C. The carrier gas was $H_2$. The amount of sample injected was 5 µL (split ratio 1:20) and the ionization energy was 70 eV. Qualitative identification of the different constituents was performed by comparison of their relative retention times and mass spectra with those of authentic reference compounds or by comparison of their retention indices and mass spectra with those shown in the literature (Adams, 1995). For this purpose, probability merge search software and the NIST MS spectra search program were used. The relative amounts (RA) of individual components of the essential oil were expressed as percentages of the peak area relative to the total peak area.

1.6 Transmission Electron Microscopy (TEM).

A dermatophyte, *Trichophyton rubrum* ($10^4$ CFU per ml), was incubated and shaken at 28° C. for 24 h in SDA medium.

The cells were recovered by centrifugation at 1500 g for 10 min at 4° C. and were washed twice with 150 mM NaCl, and then resuspended in 150 mM NaCl solution. The suspension (450 µl) of fungal cells was then mixed with a freshly prepared crude seed extract (50 µl of concentration about 2.5 mg/ml). The control solution was made without the addition of seed extract. Mixtures were then incubated for 2 h at room temperature and recovered by centrifugation at 1500 g.

The pellet was briefly fixed with 500 µl of 2.5% glutaraldehyde in 0.1M sodium cacodylate-HCl buffer at pH 7.4 and then cut into blocks of 1 mm$^3$. These cells were again fixed in 2.5% glutaraldehyde in 0.1M sodium cacodylate-HCl buffer at pH 7.4 for 2 h. After fixation, the blocks were washed several times in cacodylate buffer containing 0.1 M sucrose to remove excess fixative. Post-fixation was carried out in 1% osmium tetroxide in cacodylate buffer for 1 h at room temperature after which the blocks were washed with several changes of cacodylate buffer. The sample blocks were then dehydrated on a rotary shaker by successive soakings in 50, 70, and 90% (v/v) ethanol for 5 min each, three soakings in 100% ethanol for 10 min each and two soakings in propylene oxide for 5 min each. The dried cell blocks were then infiltrated by a mixture of epoxy resin and propylene oxide (1:1 v/v) for 1.5 h at 37° C., then by a mixture of epoxy resin and propylene oxide (3:1 v/v) overnight at room temperature, and finally by epoxy resin alone for 1h at 37° C. Following infiltration, the tissue blocks were embedded in plastic capsules (Micron Moulds), which were then polymerized at 60° C. overnight. The samples were then removed from the plastic capsules using blades and trimmed to a trapezoid shape. Ultrathin sections (90 nm) were prepared for microscopy using an ultramicrotome and were mounted on 200 mesh copper grids. Subsequently, the sections were stained in 2% aqueous uranyl acetate for 20 min, washed well with distilled water, stained in Reynold's lead citrate for 15 min and washed again with distilled water. After air-drying, TEM images of the specimens were obtained using a JEOL JE-100 SX transmission electron microscope operated at 80 kV.

2. Result And Discussion

The MICs (mg/ml) of various fractions and sub-fractions of *M. oleifera* extracts including: (1) essential oil: crude and sub-fraction EOF; (2) seed: 70% EtOH crude extract and sub-fractions, SEF, SBF and SWF; (3) leaf: 70% EtOH crude extract and sub-fractions, LEF and LWF, are shown in Table 1. The results show that both the essential oil (crude and sub-fraction of EOF) and the seeds (sub-fractions SEF and SBF) were found to have an anti-fungal effect on *Trichophyton rubrum*, *Trichophyton mentagrophytes*, *Epidermophyton floccosum* and *Microsporum canis*. The crude leaf extract and leaf sub-fractions had little effect on these dermatophytes. The sub-fractions from the crude essential oil were divided into two parts: EOF and EHF. Since EHF did not dissolve in 1% DMSO solution completely, the results shown in Table 1 do not include this sub-fraction. The crude essential oils showed different MICs on different fungi (ranging from 0.2 mg/ml (*Epidermophyton floccosum*) to 1.6 mg/ml (*Trichophyton rubrum*)). The EOF fraction shows equal ratios of MICs (ranging from 0.1 mg/ml (*Epidermophyton floccosum*) to 0.8 mg/ml (*Trichophyton rubrum*), that are exactly half the MICs recorded for the crude essential oil on these fungi. The EOF fraction had the lowest MIC (0.1 mg/ml) on *Epidermophyton floccosum*, lower than all the other extracts tested. *E. floccosum* is classified as anthropophilic dermatophyte, that is restricted to human hosts and produces a mild, chronic inflammation. It is a worldwide disease and usually infects humans via glabrous skin, the groin, hands, feet and nails. Many drugs such as ketoconozole, which is used as a control experiment in this work, can treat this disease. Although the MIC of ketoconozole (0.125~ig/m1) is lower than that of EOF (100~ig/ml), the current use of this agent is only for the optical application. The advantage of the use of BOF fraction is because it is an extract which can be developed not only optically but also orally. Also, the complex form is usually less toxic than the pure compound. Currently, the *Moringa* leaf has been orally tested by local people in Asia and Africa for many years and can be considered safe in humans. Therefore, the development of EOF fraction as an anti-dermatophyte agent via oral treatment might be a goal in the future. The cheaper source obtained from this plant for making the EOF fraction will be another advantage.

The MIC (0.156 mg/ml) of EA fraction (SEF) from 70% EtOH crude extract of *M. oleifera* seed showed the strongest anti-fungal activity of all the extracts and sub-fractions tested against *Microsporum canis*. *Microsporum canis* is classified as a zoophilic dermatophyte primarily found in animals, which causes marked inflammatory reactions in humans. The geographical distributions of the disease caused by *Microsporum canis* are North America and some areas of Europe. Infected areas usually include human beard, scalp and hair, glabrous skin and hand. Since EOF had a similarly low MIC (0.2 mg/ml) to *Microsporum canis*, both SEF and EOF extracts from *M. Oleifera* could be developed as treatment agents for *M. canis* infections. SEF and EOF in combination had less effect than either fraction individually (see Table 1). These non-additive observations may be due to the different anti-fugal compounds included in these two fractions.

Although the identification of useful constituents from each extract is beyond the scope of this paper, we analyzed the components of the essential oil of *M. oleifera* leaf as an example to be used in a detailed study in the future. A typical spectrum of gas chromatography (GC) and mass spectroscopy (MS) spectrum with the compound formulas identified is shown in FIG. 1. The GC/MS revealed a total of 41 known compounds.

The results are summarized in Table 2. In general, heneicosane (no. 41; 17.41%), (E)-phytol (no. 37; 7.66%), and 1-[2,3,6-trimethyl-phenyl]-2-butanone (no. 28; 3.44%) were the major components of the essential oil of *Moringa* leaf. Among the compounds found in the essential oil, benzaldehyde (no. 3, 0.55%) has been reported to possess anti-bacterial, anti-cancer, anti-peptic, anti-septic, anti-spasmodic and anti-tumor activities. Indole (no. 16, 1.2%) has been reported for its anti-acne, anti-bacterial, anti-cariogenic and anti-streptococcic activities. While, β-damascenone (no. 20, 0.28%) has been described to possess anti-edemic, anti-inflammatory and anti-spasmodic activities and 1-pentadecene (no. 29, 0.24%) has been shown to have anti-tumor activities. It is interesting, however, that none of the 41 known compounds has been described to have anti-fungal activity. In addition to these existing functions, a new function of anti-fungal activity might therefore be found among these known compounds. For example, as shown above, both benzaldehyde and indole have anti-bacterial functions. It is likely that they possess the anti-fungal activities. Also, they are both materials nontoxic to humans. Detailed experiments will be conducted to elucidate which of the identified compound(s) possess the anti-fungal properties in the future.

Figure 2:
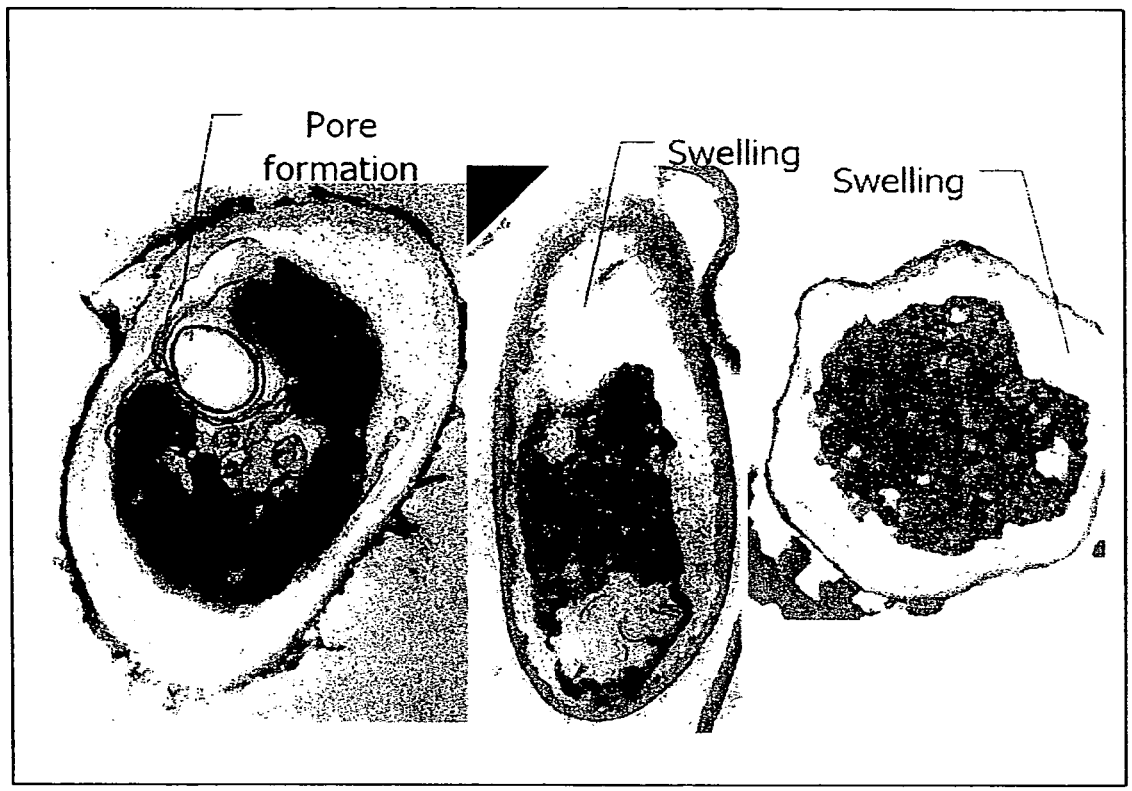
FIG. 2. Monograms of transmission electron microscopy of *Trichophyton rubrum*. TEM images of *Trichophyton*
Figure 2A:
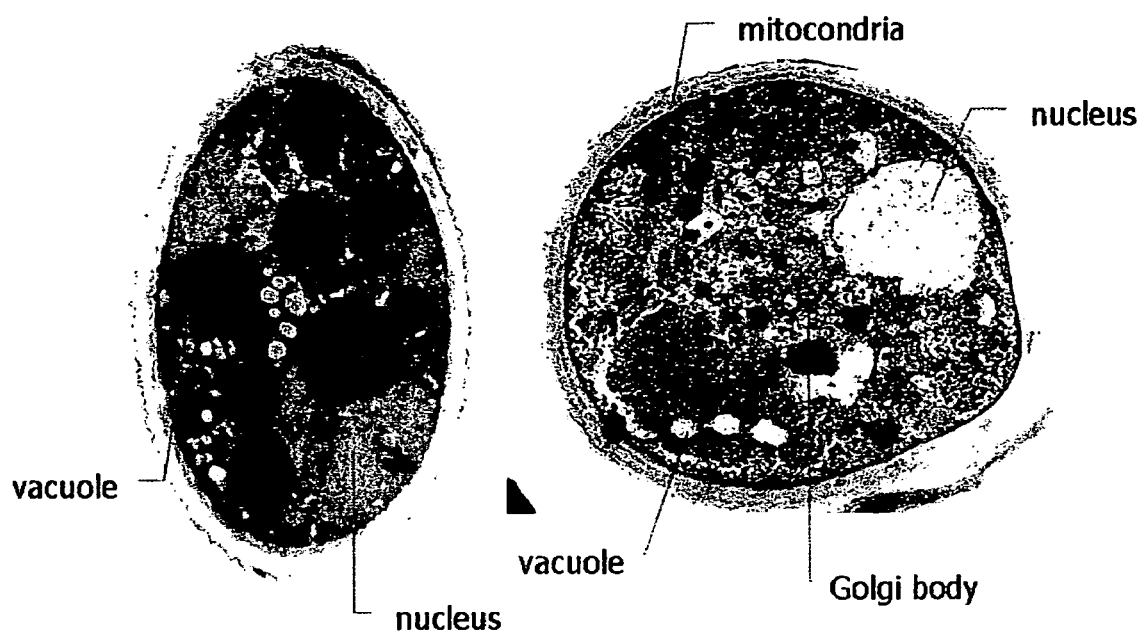
Figure 2B:
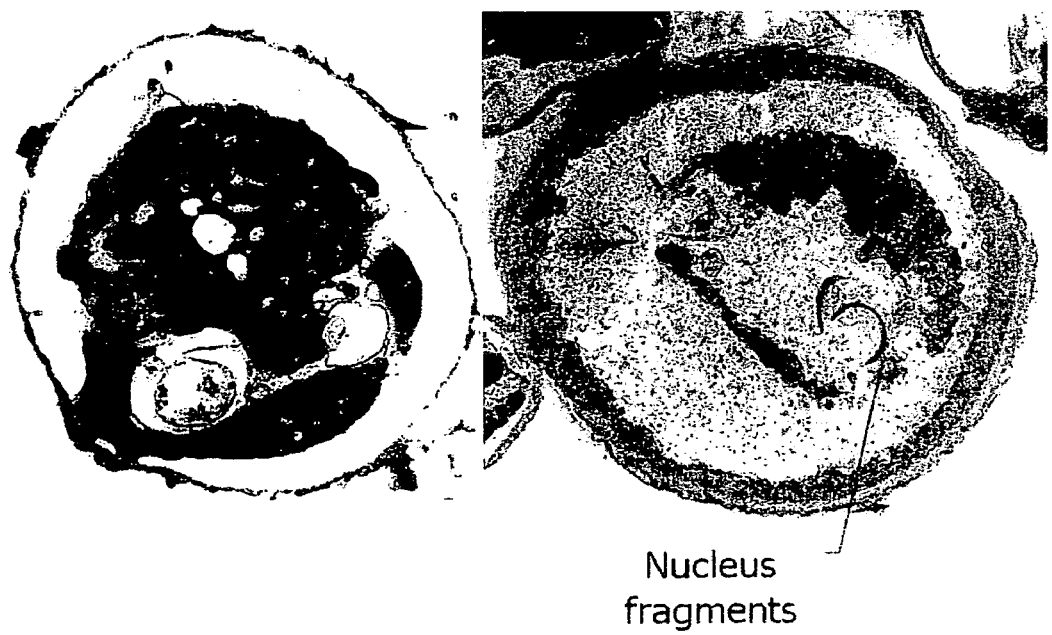

It is vitally important to know about the cell lysis mechanisms of M. Oleifera extracts on fungal cells so that further development of disease treatment can be conducted accordingly. A study of the morphological change of the cell induced by these extracts would therefore be the preliminary in understanding the lysis mechanism. In this experiment, we used M. Oleifera seed crude extract as an example to study the shape change of Trichophyton rubrum cells using transmission electron microscopy (TEM). FIG. 2 shows TEM images of fungal cells, which were treated with 70% EtOH crude extract of M. oleifera seed for 24 h. The results show that the cytoplasmic membrane of the fungal cell was ruptured and the intracellular components were seriously damaged after treatment with seed crude extract (see FIG. 2b). However, the intracellular components did not leak out. Based on our previous studies of the cell lysis pathways of anti-microbial peptides on bacteria using TEM and immuno-gold TEM (Chan et al., 1998; Chen et al., 2003), this might indicate that extract compounds interact with the lipid bilayers in membranes leading to the subsequent separation (see FIG. 2c) of the two membranes (outer and inner membranes). Water then transvases between two membranes causing the cell to swell (Chen et al., 2003) leading to cell death. A detailed study of the mechanisms induced by M. Oleifera crude extracts to kill fungal cells will be conducted in the near future.

Based on the observations above, we found that M. oleifera leaf essential oil and its seed extract can be partitioned and possess antifungal properties. The fractions of EOF and SEF are potent for all dermatophytes used in this experiment.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

REFERENCES

1. Beentje, H. J., 1994. Moringaceae. In Kenya Trees Shrub and Lianas. Majestic Printing Works LTD, Nairobi, Kenya, Chapter 37.
2. Vlahof, G., Chepkwony, P. K., Ndalut, P. K., 2002. $^{13}$C NMR Characterization of Triacylglycerols of Moringa oleifera Seed Oil: An "Oleic-Vaccenic Acid" Oil. Journal of agricultural and food chemistry 50, pp 970-975.
3. Nesainani, 5., 1999. Medicinal Plants. State Institute of Languages, Thiruvananthapuram, Kerala, India, Vol I, p. 425.
4. Ezeamuzle, I. C., Ambadederomo, A. W., Shode, F. O. Ekwebelem, S. C., 1996. Antiinflammatory effects of Moringa oleifera root extract. International Journal of Pharmacognosy 34, pp 207-212.
5. Pan L., Kumar N. A., 2002. Hepatoprotective activity of Moringa oleifera on antitubercular drug-induced liver damage in rats. Journal of Medicinal Food 5(3), pp 171-177.
6. Faizi, S., Siddiqui, B. S., Saleem, R., Siddiqui, S., Aftab, K., Gilani, A. H., 1995. Fully acetylated carbonate and hypotensive thiocarbamate glycosides from Moringa oleifera. Phytochemistry 38, pp 957-963.
7. Murakami, A., Kitazono, Y., Jiwajinda, S., Koshimizu, K., Ohigashi, H., 1998. Niaziminin, a thiocarbamate from the leaves of Moringa olefera, holds a strict structural requirement for inhibition of tumor-promoter-induced Epstein-Barr virus activation. Planta Medica 64, pp 319-323.
8. Eilert, U., Wolters, B., Nahrstedt, A., 1981. The antibiotic principle of seeds of Moringa oleifera and Moringa stenopetala. Planta Medica 42, pp 55-61.
9. Tsaknis, J., Lalas, S., Gergis, V., Dourtoglou, V., Spilotis, V., 1999. Characterisation of Moringa oleifera variety Mbololo seed oil of Kenya. Journal of agricultural and food chemistry 47, pp 4495-4499.
10. Tahiliani, P., Kar, A., 2000. Role of Moringa oleifera leaf extract in the regulation of thyroid hormone status in adult male and female rats. Pharmacological Research 41, pp 319-323.
11. Ghasi, S., Nwobobo, E., Ofili, J. O. 2000. Hypocholesterolemic effects of crude extract of leaf of Moringa oleifera Lam in high-fat diet fed Wistar rats. Journal of Ethnopharmacology 69, pp 2 1-25.
12. Brophy, J. J., House, A. P. N., Bolandand, D. J., Lassak, E. V., 1991. Digests of the essential oil of III species from northern and eastern Australia in Eucalytpus Leaf Oils— Use chemistry distillation and marketing. Inkata Press. Melbourne/Sydney.
13. Adams, R. P., 1995. Identification of Essential Oil Components by Gas Chromatography/Mass Spectroscopy; Allured Publishing: Carol Stream, Ill.
14. Chan, S. C., Yau, W. L., Wang, W., Smith, D., Sheu, F. S., Chen, H. M., 1998. Microscopic observations of the different morphological changes by the anti-bacterial peptides on Klebsiella pneumomae and HL-60 leukemia cells. Journal of Peptide Science 4, pp 4 13-425.
15. Chen, H. M., Chan, S. C., Lee, J. C., Chang, C. C., Murugan, M., Jack, R. J., 2003. Transmission electron microscopic observations of membrane effects of antibiotic cecropin B on Escherichia coli. Microscopy Research and Technique 62, pp 423-430.

TABLE 1

Minimum inhibitory concentration (MIC) of M. Oleifera extracts against specific fungi. The dermatophytes used were trichophyton rubrum, trichophyton mentagrophytes, epidermophyton floccusm and microsporum canis. The M. oleifera extracts or sub-fractions used were collected from the essential oil, seed and leaf. MIC values used were in mg/ml.

|  | essential oil | | seed | | | | leaf | | | |
| --- | --- | --- | --- | --- | --- | --- | --- | --- | --- | --- |
|  | crude*[1] | EOF | extract*[2] | SEF | SBF | SWF | extract*[2] | LEF | LWF | EOF + SEF*[3] |
| *Trichophyton rubrum* | 1.6 | 0.8 | 2.5 | 0.625 | 2.5 | >10 | >10 | >10 | >10 | 0.8 |
| *Tricophyton mentagrophytes* | 0.8 | 0.4 | 2.5 | 1.25 | 2.5 | >10 | >10 | >10 | >10 | 1.6 |
| *Epidermophyton floccusum* | 0.2 | 0.1 | 2.5 | 0.625 | 2.5 | >10 | >10 | >10 | >10 | 0.8 |
| *Microsporum canis* | 0.4 | 0.2 | 2.5 | 0.156 | 2.5 | >10 | >10 | >10 | >10 | 1.6 |

*[1] essential oil before partition;
*[2] 70% EtOH crude extract;
*[3] EOF:SEF = 1:1 (w/w)

TABLE 2

Constituents of the essential oil of M. oleifera leaf. The known compounds included in the essential oil of M. oleifera leaf were referenced and identified by GC/MS spectrum and the NIST MS spectra search program (see text for details). These compounds have been characterized and some are discussed in the text.

| No. | Component | RT*[1] | % RA*[2] |
| --- | --- | --- | --- |
| 1 | toluene | 3.76 | 0.03 |
| 2 | 5-tert-butyl-1,3-cyclopentadiene | 5.90 | 0.07 |
| 3 | benzaldehyde | 13.16 | 0.55 |
| 4 | 5-methyl-2-furaldehyde | 13.69 | 0.27 |
| 5 | benzeneacetaldehyde | 22.22 | 2.16 |
| 6 | 2-ethyl-3,6-dimethylpyrazine | 25.67 | 0.12 |
| 7 | undecane | 27.79 | 0.12 |
| 8 | α-isophoron | 29.06 | 0.10 |
| 9 | benzylnitrile | 30.94 | 1.10 |
| 10 | 2,6,6-trimethyl-2-cyclohexane-1,4-dione | 31.28 | 0.05 |
| 11 | 2,2,4-trimethyl-pentadiol | 32.03 | 0.09 |
| 12 | 2,3-epoxycarane | 34.41 | 0.16 |
| 13 | p-menth-1-en-8-ol | 35.04 | 0.08 |
| 14 | 2,6,6-trimethylcyclohexa-1,3-dienecarbaldehyde | 35.63 | 0.23 |
| 15 | dodecane | 36.10 | 0.05 |
| 16 | indole | 42.68 | 1.20 |
| 17 | tridecane | 43.62 | 0.16 |
| 18 | 1,1,6-trimethyl-1,2-dihydronaphthalene | 46.52 | 0.41 |
| 19 | α-ionene | 46.78 | 0.09 |
| 20 | β-damascenone | 48.90 | 0.28 |
| 21 | tetradecane | 50.31 | 0.12 |
| 22 | 2-tert-butyl-1,4-dimethoxybenzene | 51.66 | 0.39 |
| 23 | (E)-6,10-dimethylundeca-5,9-dien-2-one | 53.42 | 0.26 |
| 24 | 4,6-dimethyl-dodecane | 54.02 | 0.29 |
| 25 | 3,3,5,6-tetramethyl-1-indanone | 56.69 | 0.23 |
| 26 | dihydro-actiridioide | 57.60 | 1.21 |
| 27 | 2,3,6-trimethyl-naphthalene | 59.36 | 0.37 |
| 28 | 1-[2,3,6-trimethyl-phenyl]-2-butanone | 61.04 | 3.44 |
| 29 | pentadecane | 62.21 | 0.24 |
| 30 | 1-[2,3,6-trimethyl-phenyl]-3-buten-2-one | 62.70 | 0.75 |
| 31 | isolongifolene | 63.29 | 0.56 |
| 32 | hexahydrofarnesylactone | 79.93 | 1.30 |
| 33 | farnesylacetone | 85.00 | 0.08 |
| 34 | methyl palmitate | 85.77 | 0.08 |
| 35 | n-hexadecanoic acid | 88.62 | 1.08 |
| 36 | [6E,10E]-7,11,15-trimethyl-methylene-1,6,10,14-hexadeca-tetraene | 91.71 | 0.11 |
| 37 | (E)-phytol | 96.55 | 7.66 |
| 38 | octadecane | 100.69 | 0.28 |
| 39 | 1-pentadecene | 109.23 | 0.41 |
| 40 | 10-methyl-eicosane | 109.51 | 1.45 |
| 41 | heneicosane | 114.52 | 17.41 |

*[1] RT indicates the retention time on the column in minutes.
*[2] RA indicates relative area (peak area relative to the total peak area).

We claim:

1. A method of treating a fungal infection in a subject by administering to the subject a pharmaceutical composition comprising the oxygenated fraction (EOF) of essential oil extract from the leaf of *M. oleifera* as the sole active component.

2. The method of claim 1, wherein the pharmaceutical composition is administered orally, topically or occularly.

3. The method of claim 1, wherein the fungal infection is caused by a fungus selected from the group consisting of *T. rubrum, T. mentagrophytes, E. floccosum* and *M. canis*.

4. The method of claim 1, wherein the fungal infection is caused by *E. floccosum*.

5. The method of claim 1, wherein the subject is human.

* * * * *